US 6,577,896 B2

(12) United States Patent
Werner et al.

(10) Patent No.: US 6,577,896 B2
(45) Date of Patent: Jun. 10, 2003

(54) SINGLE COMPLEX ELECTROGRAM DISPLAY HAVING A SENSING THRESHOLD FOR AN IMPLANTABLE MEDICAL DEVICE

(75) Inventors: Robert Werner, Minnetonka, MN (US); Jack P. Krichen, Fridley, MN (US); Deborah Sackrison, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 142 days.

(21) Appl. No.: 09/780,860

(22) Filed: Feb. 9, 2001

(65) Prior Publication Data

US 2001/0031927 A1 Oct. 18, 2001

Related U.S. Application Data

(62) Division of application No. 09/316,750, filed on May 21, 1999, now Pat. No. 6,266,555.
(60) Provisional application No. 60/084,580, filed on May 7, 1998.

(51) Int. Cl.[7] ............................................... A61B 5/044
(52) U.S. Cl. ........................................ 600/523; 607/27
(58) Field of Search ..................... 607/27, 30; 600/523, 600/522, 509

(56) References Cited

U.S. PATENT DOCUMENTS

| | | | |
|---|---|---|---|
| 2,655,425 A | * 10/1953 | Wood ...................... 200/19.01 |
| 4,316,472 A | 2/1982 | Mirowski et al. ....... 128/419 D |
| 4,374,382 A | 2/1983 | Markowitz ............. 340/870.01 |
| 4,375,817 A | 3/1983 | Engle et al. ............ 128/419 D |
| 4,379,459 A | 4/1983 | Stein ...................... 128/419 PG |
| 4,384,585 A | 5/1983 | Zipes ...................... 128/419 D |
| 4,476,868 A | 10/1984 | Thompson ............. 128/419 PG |
| 4,483,346 A | * 11/1984 | Slavin .................... 346/33 ME |
| 4,556,063 A | 12/1985 | Thompson et al. .... 128/419 PT |
| 4,577,633 A | 3/1986 | Berkovits et al. ..... 128/419 PG |
| 4,587,970 A | 5/1986 | Holley et al. ......... 128/419 PG |
| 4,726,380 A | 2/1988 | Vollmann et al. ..... 128/419 PG |
| 4,727,877 A | 3/1988 | Kallok .................... 128/419 D |
| 4,779,100 A | * 10/1988 | Voelz ..................... 346/33 ME |

(List continued on next page.)

FOREIGN PATENT DOCUMENTS

WO            9218198           10/1992        ............ A61N/1/05

OTHER PUBLICATIONS

Olson et al "Onset and Stability for Ventricular Tachyarrhythmia Detection in an Implantable Pacer–Cardioverter–Defibrillator" Oct. 7–10, 1986 pp. 167–170 Computers in Cardiology, IEEE, Computer Society Press.
Arzbaecher "Automatic Tachycardia Recognition" May –Jun. 1984, pp. 541–547, PACE.

*Primary Examiner*—Kennedy Schaetzle
(74) *Attorney, Agent, or Firm*—Girma Wolde-Michael

(57) ABSTRACT

The present invention discloses a graphical display method and apparatus relating to an electrogram signal received from at least one lead used in conjunction with an implantable medical device. The present invention provides a time-expanded waveform of a portion of a signal relating to a single heartbeat. Sensitivity threshold information is also graphically displayed on the waveform. The programmer assembly of the present invention comprises an analyzer for locating and marking desired characteristics of the electrogram signal with a plurality of markers to produce a marked electrogram signal. A processor receives the electrogram signal from the analyzer and recognizes the marked desired characteristics of the electrogram signal. The processor also receives sensitivity threshold information from a particular lead. A display, controlled by the processor, graphically displays information representing a portion of the electrogram signal immediately adjacent to a single marker and graphically displays a sensitivity threshold superimposed onto the portion of the electrogram signal.

31 Claims, 13 Drawing Sheets

U.S. PATENT DOCUMENTS

| | | |
|---|---|---|
| 4,800,883 A | 1/1989 | Winstrom .................. 128/419 D |
| 4,809,697 A | 3/1989 | Causey, III et al. ... 128/419 PT |
| 4,821,723 A | 4/1989 | Baker, Jr. et al. ....... 128/419 D |
| 4,830,006 A | 5/1989 | Haluska et al. ........ 128/419 PG |
| 4,880,005 A | 11/1989 | Pless et al. ........... 128/419 PG |
| 4,949,719 A | 8/1990 | Pless et al. .............. 128/419 D |
| 4,953,551 A | 9/1990 | Mehra et al. ........... 128/419 D |
| 5,099,838 A | 3/1992 | Bardy ..................... 128/419 D |
| 5,117,824 A | 6/1992 | Keimel et al. .......... 128/419 D |
| 5,127,404 A | 7/1992 | Wyborny et al. ........ 128/419 P |
| 5,131,388 A | 7/1992 | Pless et al. .............. 128/419 D |
| 5,144,949 A | 9/1992 | Olson ................... 128/419 PG |
| 5,158,078 A | 10/1992 | Bennett et al. ........ 128/419 PG |
| 5,163,427 A | 11/1992 | Keimel ................... 128/419 D |
| 5,188,105 A | 2/1993 | Keimel ................... 128/419 D |
| 5,199,428 A | 4/1993 | Obel et al. .............. 128/419 C |
| 5,207,218 A | 5/1993 | Carpentier et al. ... 128/419 PG |
| 5,269,298 A | 12/1993 | Adams et al. ........... 128/419 D |
| 5,292,343 A | 3/1994 | Blanchette et al. ........... 607/32 |
| 5,312,453 A | 5/1994 | Shelton et al. ................. 607/19 |
| 5,314,430 A | 5/1994 | Bardy ........................... 607/5 |
| 5,330,507 A | 7/1994 | Schwartz ...................... 607/14 |
| 5,331,966 A | 7/1994 | Bennett et al. .............. 128/696 |
| 5,344,431 A | 9/1994 | Merritt et al. ................. 607/29 |
| 5,345,362 A | 9/1994 | Winkler ..................... 361/681 |
| 5,354,316 A | 10/1994 | Keimel ......................... 607/15 |
| 5,354,319 A | 10/1994 | Wyborny et al. .............. 607/32 |
| 5,374,282 A | 12/1994 | Nichols et al. ................ 607/18 |
| 5,402,794 A | 4/1995 | Wahlstrand et al. ........ 128/696 |
| D358,583 S | 5/1995 | Winkler ..................... D14/106 |
| 5,545,186 A | 8/1996 | Olson et al. ................... 607/14 |
| 5,620,473 A * | 4/1997 | Poore ........................... 607/27 |
| 5,690,686 A | 11/1997 | Min et al. ....................... 607/5 |
| 5,713,937 A | 2/1998 | Nappholz et al. .............. 607/30 |
| 5,716,384 A | 2/1998 | Snell ............................ 607/30 |
| 5,724,985 A | 3/1998 | Snell et al. .................. 128/697 |
| 5,782,890 A | 7/1998 | Wahlstrand et al. ........... 607/32 |
| 5,800,465 A | 9/1998 | Thompson et al. ............. 607/9 |
| 5,833,623 A | 11/1998 | Mann et al. ................. 600/523 |
| 5,836,889 A | 11/1998 | Wyborny et al. ........... 600/509 |
| 5,891,169 A | 4/1999 | Boheim et al. ................. 607/4 |

* cited by examiner

SINGLE COMPLEX ELECTROGRAM DISPLAY HAVING A SENSING THRESHOLD FOR AN IMPLANTABLE MEDICAL DEVICE

This application is a division of application Ser. No. 09/316,750, filed May 21, 1999, now U.S. Pat. No. 6,266, 555. This application claims the benefit of U.S. provisional application Ser. No. 60/084,580, filed May 7, 1998.

FIELD OF THE INVENTION

The present invention relates generally to a programmer used in conjunction with an implantable medical device. More specifically, the present invention relates to an improved graphical display of selected information in conjunction with an implantable medical device.

BACKGROUND OF THE INVENTION

Implantable medical device systems known in the art comprise several components, including an implantable medical device, such as a pacemaker, pacing and/or sensing leads (leads), and a programmer. The leads connect the implantable medical device to the heart of a patient. The programmer provides multiple functions, including (a) assessing lead performance during a pacemaker or defibrillator implantation, (b) programming the implantable medical device, and (c) receiving feedback information from the implantable medical device for use by a clinician or physician (operator). By measuring the electrical performance of a lead, the programmer aids the operator in selecting an electrically appropriate site for the placement of the lead(s).

In conjunction with programming the implantable medical device system, it is critical for an operator to determine whether the leads are properly positioned within a passageway of a heart, such as an atrium or ventricle of the patient.

A disadvantage of prior art programmers involves the techniques used to display information to the operator during an implant procedure. Most prior art systems graphically display several, continuous-time waveforms, which are constantly scrolling across the screen at a rapid rate. The remaining information is presented to the operator in the form of numerical data. In order to determine if a specific lead is properly positioned within a passageway of the heart, the operator must review not only the graphical display of the continuous-time cardiac waveform scrolling across the display, but also review a variety of numerical data. The operator must then have the ability and understanding to process the various data shown both graphically and numerically in order to determine if the lead is positioned to ensure proper operation of a later attached implantable medical device.

U.S. Pat. No. 5,713,937 to Nappholz et al. discloses a pacemaker programmer menu with selectable real or simulated implant data graphics. This reference discloses a graphical display of two separate characteristics of an implantable medical device system, such as a heartbeat of a patient and a ventricular pacing rate as applied to a medical implant.

Other disclosures relating to the same general issues are listed below in Table 1.

TABLE 1
Prior Art Patents

| U.S. Pat. No. | Title |
| --- | --- |
| 5,833,623 | System And Method For Facilitating Rapid Retrieval And Evaluation Of Diagnostic Data Stored By An Implantable Medical Device |
| 5,782,890 | Method For Heart Transplant Monitoring And Analog Telemetry Calibration |
| 5,724,985 | User Interface For An Implantable Medical Device Using An Integrated Digitizer Display Screen |
| 5,716,384 | Method And System For Organizing, Viewing And Manipulating Information In Implantable Device Programmer |
| 5,402,794 | Method And Apparatus For Heart Transplant Monitoring And Analog Telemetry Calibration |
| 5,374,282 | Automatic Sensitivity Adjust For Cardiac Pacemakers |
| 5,345,362 | Portable Computer Apparatus With Articulating Display Panel |
| 4,809,697 | Interactive Programming And Diagnostic System For Use With Implantable Pacemaker |
| 4,374,382 | Marker Channel Telemetry System For A Medical Device |
| Des. 358,583 | Portable Computer With An Articulating Display Panel |

The prior art in general, as well as the Nappholz et al. reference in particular, have certain disadvantages. For example, the display units of the prior art patents display a continuous-time cardiac waveform. This waveform is continuously scrolling across the display. Once the continuous-time waveform reaches the end of the display, the waveform disappears and a new continuous-time waveform is generated in real time and scrolls across the screen. Thus, it is virtually impossible for an operator to determine the configuration of the waveform signal, or to determine the amplitude of the signal. Additionally, the operator must evaluate various numerical data in conjunction with the graphical display to determine if a specific lead is properly positioned.

SUMMARY OF THE INVENTION

The present invention overcomes the disadvantages of the prior art by providing a method of and apparatus for graphically displaying a visual assessment necessary to determine proper positioning of pacing and/or sensing leads of an implantable medical device system.

The present invention has certain objects. That is, the present invention provides solutions to certain problems existing in the prior art such as: (a) an inability to provide a graphical display of a single cardiac waveform representing a specific portion of the continuous-time waveform corresponding to a single heartbeat, centered on the display; (b) an inability to update the single cardiac waveform based upon a comparison of the heart rate of the patient to specific predetermined rates; (c) an inability to provide a graphical display of the magnitude of the single cardiac waveform; (d) an inability to provide the graphical display of a chosen sensitivity threshold in conjunction with a single cardiac waveform; (e) an inability to provide a graphical display of changes in the sensitivity threshold in conjunction with a single cardiac waveform; (f) an inability to hold the single cardiac waveform, centered on the display; and (g) an inability to print the single cardiac waveform.

The system and method of the present invention provides certain advantages, including: (a) the ability to provide a graphical display of a single cardiac waveform representing a specific portion of the continuous-time waveform corresponding to a single heartbeat centered on the display; (b) the ability to update the cardiac waveform based upon a comparison of the heart rate to specific predetermined rates; (c) the ability to provide a graphical display of the magnitude of the single cardiac waveform; (d) the ability to provide a graphical display of a chosen sensitivity threshold in conjunction with a single cardiac waveform; (e) the ability to provide a graphical display of changes in the sensitivity threshold in conjunction with a single cardiac waveform; (h) the ability to hold the single cardiac waveform centered on the display; and (i) the ability to print the single cardiac waveform.

The system and method of the present invention has certain features, including a graphical display of a single cardiac waveform representing a specific portion of the continuous-time waveform corresponding to a single heartbeat at a time during a pacemaker implant. In addition, the present invention permits selection of the heart passageway from which to view the waveform. Another feature of the present invention is a graphical display of the voltage magnitude of the single cardiac waveform, as well as an expanded version of the single cardiac waveform used to determine the proper position of a lead. Another feature of the present invention is the ability to utilize the heart rate of the patient such that the single cardiac waveform is continuously updated in a manner in which an operator can view the waveform to determine proper location of a pacing or sensing lead. Another feature of the present invention is a graphical representation of a chosen sensing threshold superimposed onto a single cardiac waveform to assist in positioning of a pacing or sensing lead. Another feature of the present invention is the ability to graphically display an updated and modified sensing threshold. Another feature of the present invention is the ability to freeze the single cardiac waveform and superimposed sensing threshold and print a single cardiac waveform and superimposed sensing threshold for further analysis.

Other objects, advantages, and features of the invention will become apparent by referring to the appended drawings, detailed description, and claims.

DETAILED DESCRIPTION

In the following detailed description of the preferred embodiments, reference is made to the accompanying drawings which form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
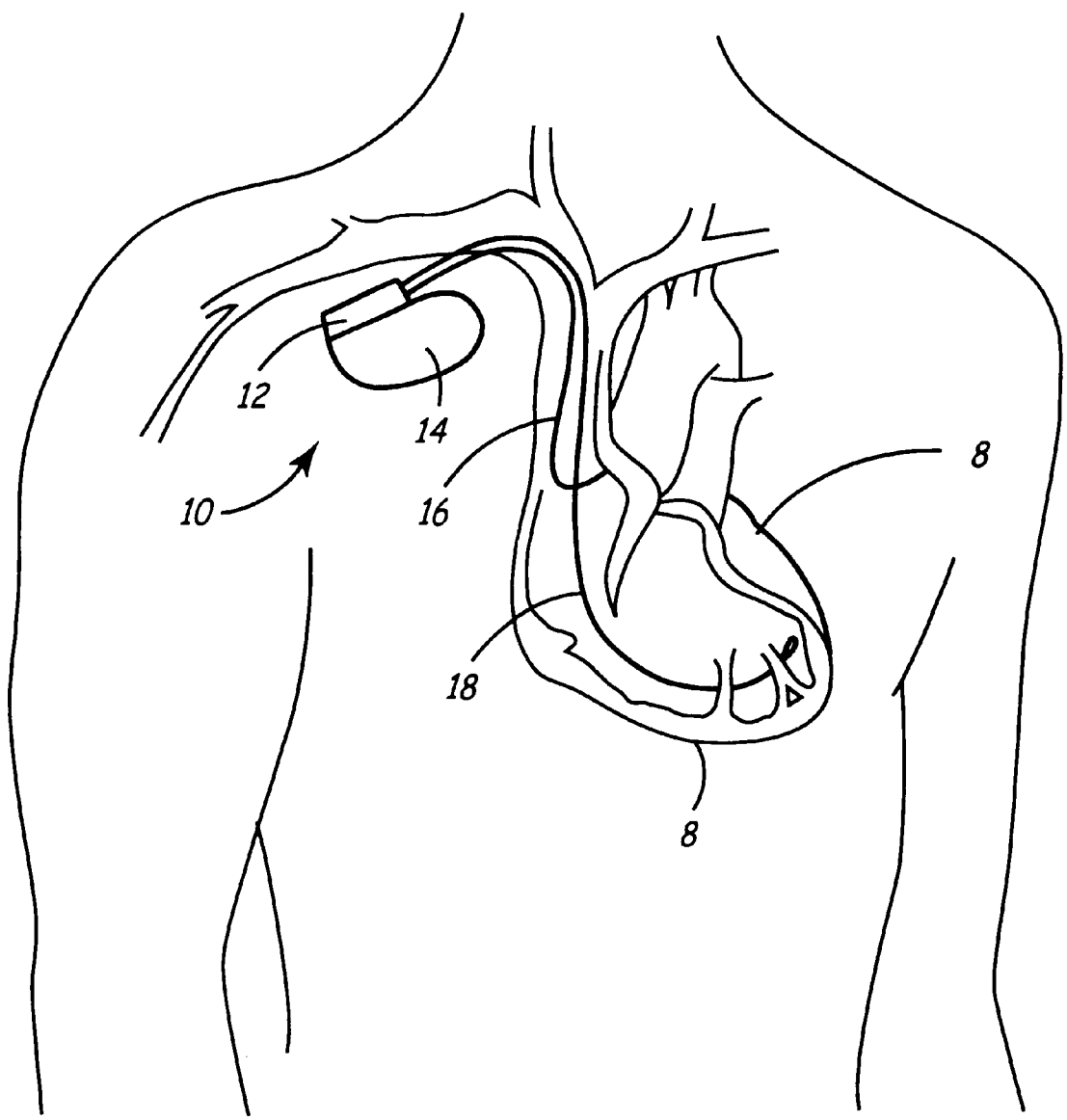
FIG. 1 is a simplified schematic view of one embodiment of an implantable medical device.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to connector module 12 of hermetically sealed enclosure 14 and implanted near human or mammalian heart 8. Pacing and sensing leads 16 and 18 sense electrical signals attendant to the depolarization and repolarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al., or U.S. Pat. No. 5,144,949 to Olson, all hereby incorporated by reference herein, each in its respective entirety.

Figure 2:
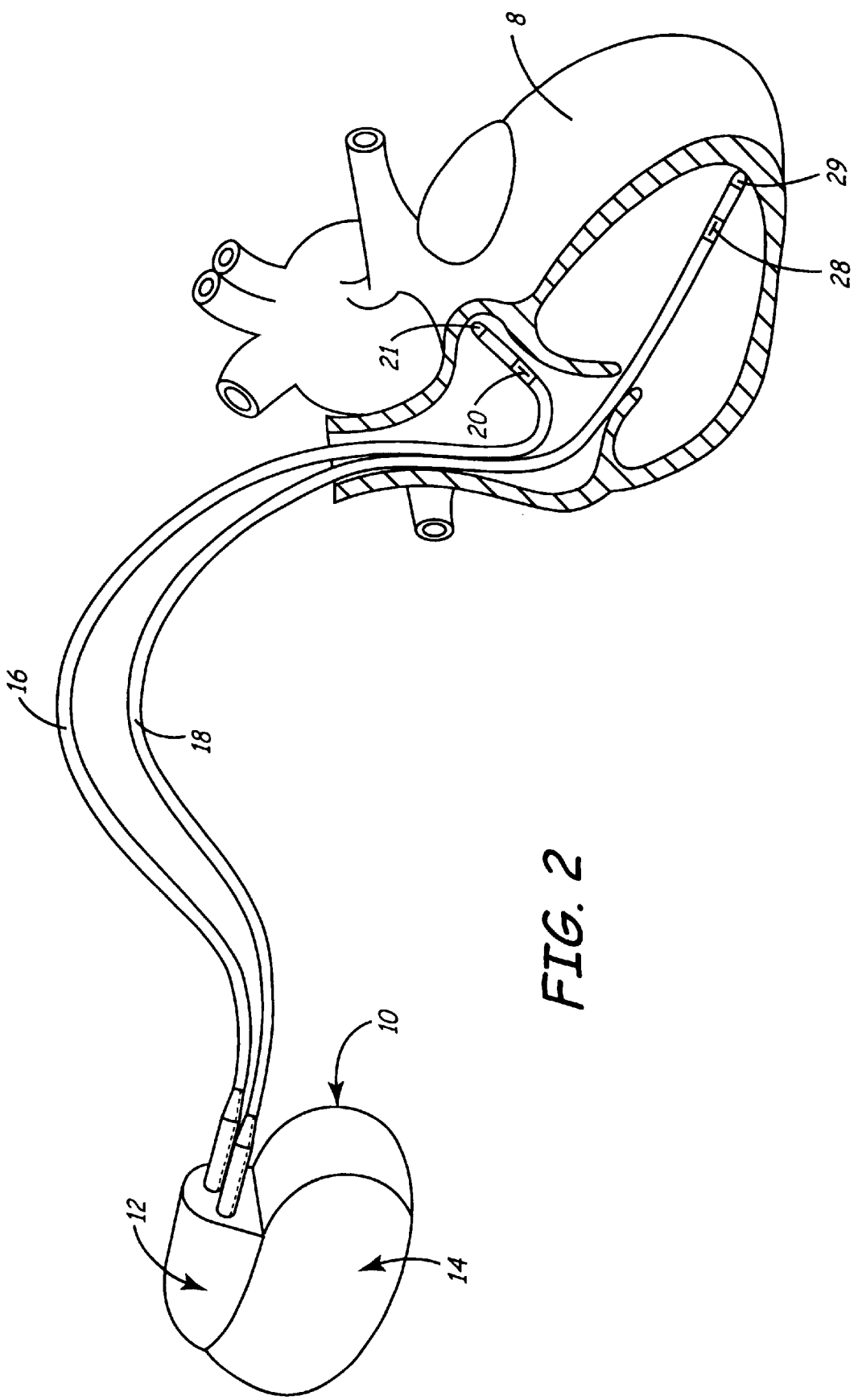
FIG. 2 is a simplified illustration of an implantable medical device with leads positioned within passageways of a heart.

FIG. 2 shows connector module 12 and hermetically sealed enclosure 14 of IMD 10 located in and near human or mammalian heart 8. Atrial and ventricular pacing leads 16 and 18 extend from connector module 12 to the right atrium and ventricle, respectively, of heart 8. Atrial electrodes 20 and 21 disposed at the distal end of atrial pacing lead 16 are located in the right atrium. Ventricular electrodes 28 and 29 disposed at the distal end of ventricular pacing lead 18 are located in the right ventricle.

Figure 3:
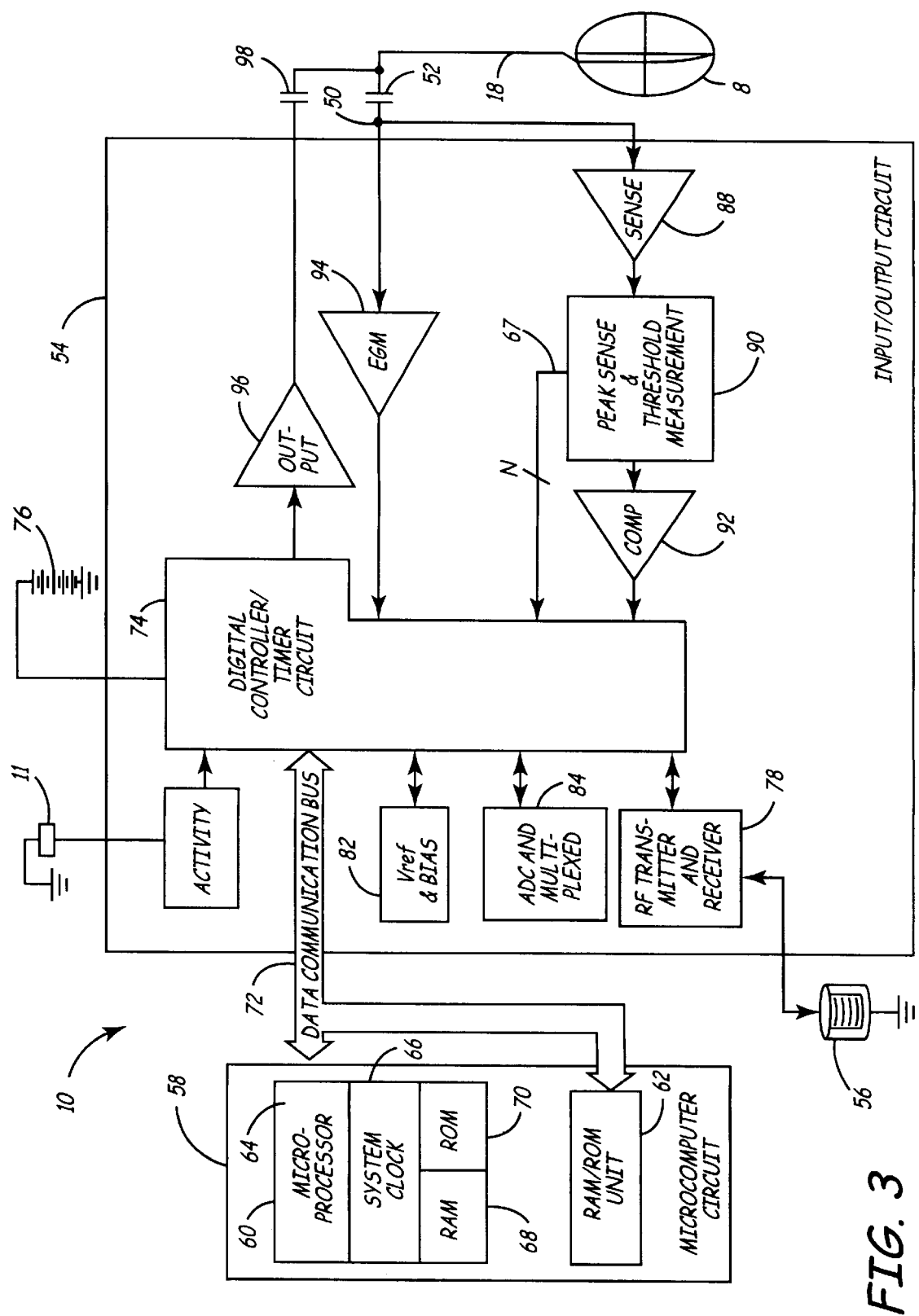
FIG. 3 is a block diagram illustrating the constituent components of an implantable medical device.

FIG. 3 shows a block diagram illustrating the constituent components of IMD 10 in accordance with one embodiment of the present invention, where IMD 10 is a pacemaker having a microprocessor-based architecture. IMD 10 is shown as including activity sensor or accelerometer 11, which is preferably a piezoceramic accelerometer bonded to a hybrid circuit located inside enclosure 14 (shown in FIGS. 1 and 2). Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto. However, it is understood that similar circuitry and connections not explicitly shown in FIG. 3 apply to lead 16 (shown in FIGS. 1 and 2).

Figure 6:
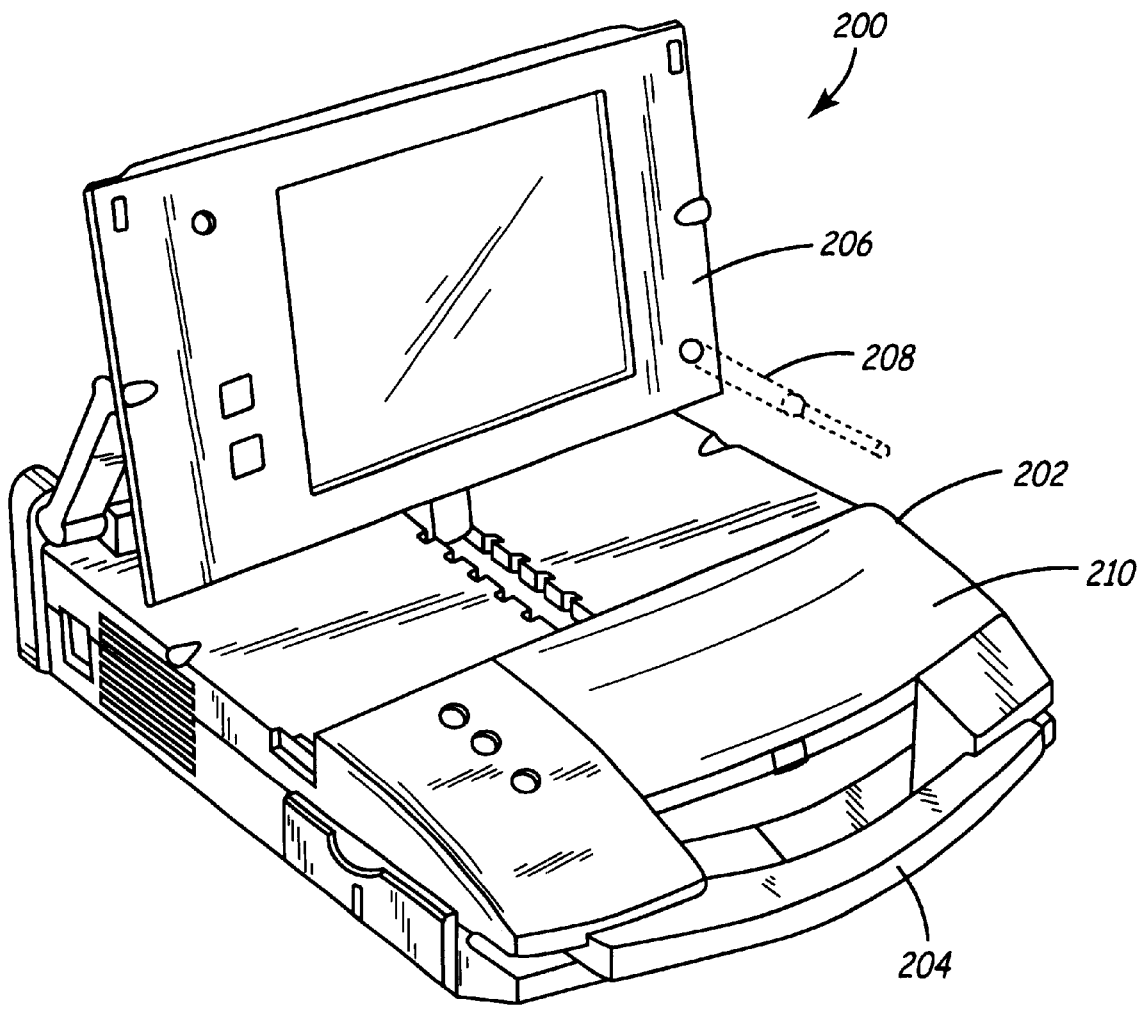
FIG. 6 is a perspective view of a programmer unit used in conjunction with an implantable medical device.

IMD 10 in FIG. 3 is most preferably programmable by means of an external programming unit (shown in FIG. 6).

One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing with heart 8, activity sensor 11, antenna 56 and circuits for the application of stimulating pulses to heart 8. The rate of heart 8 is controlled by software-implemented algorithms stored within microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures.

Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled from microprocessor 64 via data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is also provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides amplified pacing stimuli to patient's heart 8 through coupling capacitor 98 in response to a pacing trigger signal provided by digital controller/timer circuit 74 each time either (a) the escape interval times out, (b) an externally transmitted pacing command is received, or (c) in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of sense amplifier 88, output pulse generator 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive modes, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with one or more leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, and U.S. Pat. No. 4,821,723 to Baker et al., all hereby incorporated by reference herein, each in its respective entirety.

Figure 4:
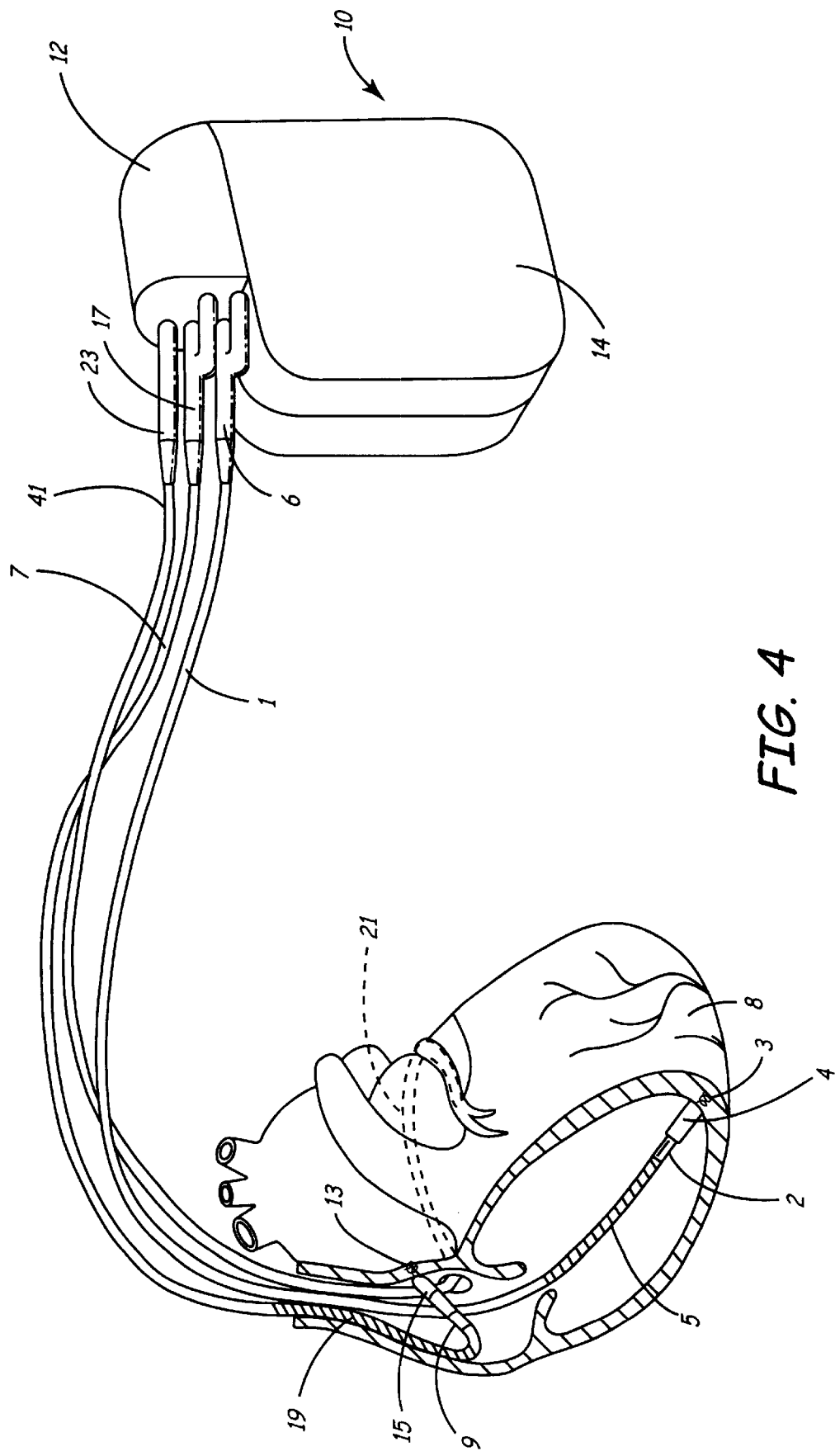
FIG. 4 is a simplified schematic view of an implantable medical device with leads positioned within passageways of a heart.
Figure 5:
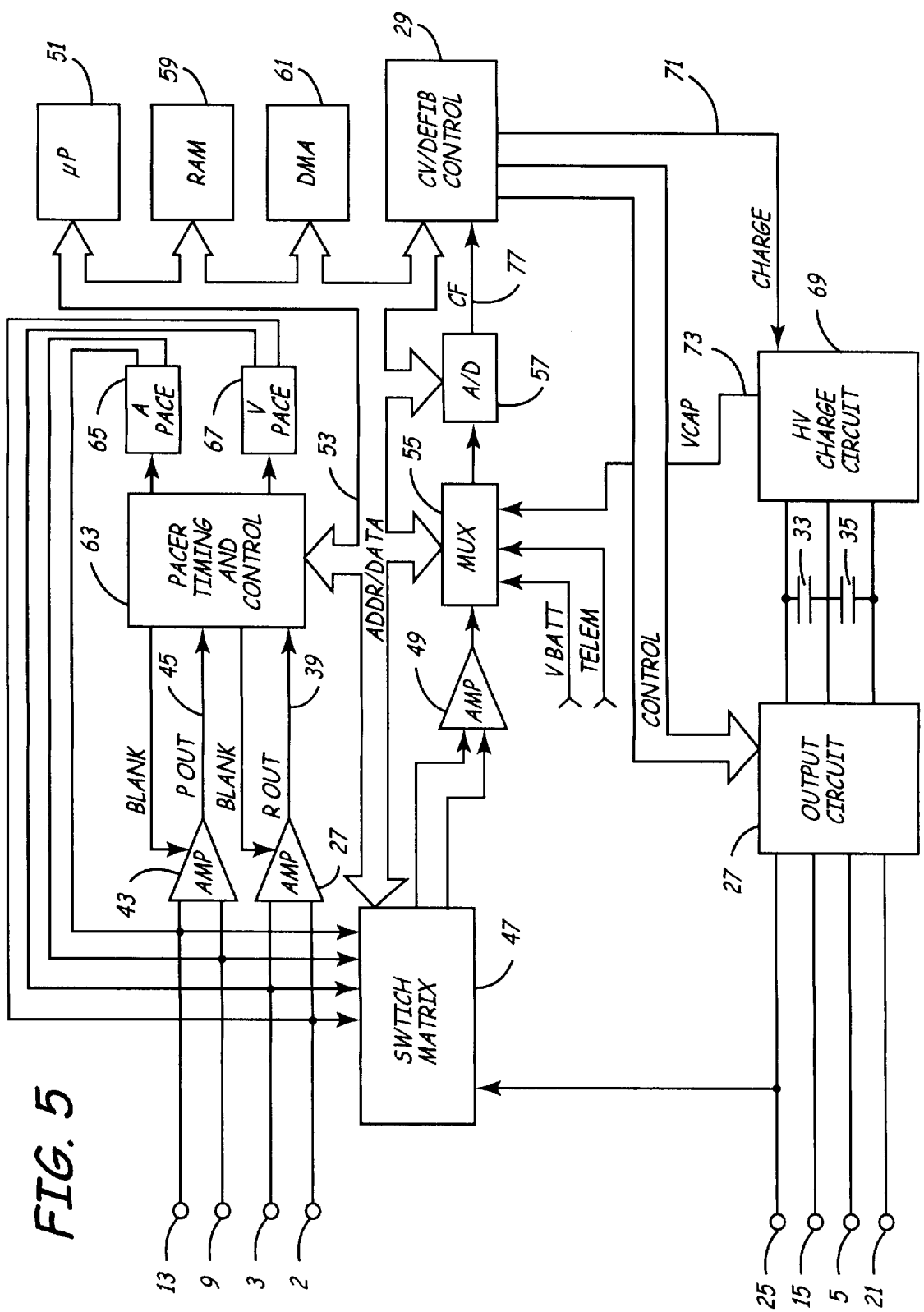
FIG. 5 is a partial block diagram illustrating one embodiment of an implantable medical device used in conjunction with the present invention.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 100 carrying three concentric coiled conductors separated from one another by tubular insulative sheaths. Located adjacent the distal end of lead 100 are ring electrode 102, extendable helix electrode 104 mounted retractably within insulative electrode head 106 and elongated coil electrode 108. Each of the electrodes is coupled to one of the coiled conductors within lead body 100. Electrodes 102 and 104 are employed for cardiac pacing and for sensing ventricular depolarizations. At the proximal end of the lead is bifurcated connector 110 which carries three electrical connectors, each coupled to one of the coiled conductors. Elongated coil electrode 108, which is a defibrillation electrode 108, may be fabricated from platinum, platinum alloy or other materials known to be usable in implantable defibrillation electrodes and may be about 5 cm in length.

The atrial/SVC lead shown in FIG. 4 includes elongated insulative lead body 112 carrying three concentric coiled conductors separated from one another by tubular insulative sheaths corresponding to the structure of the ventricular lead. Located adjacent the J-shaped distal end of the lead are ring electrode 114 and extendable helix electrode 116 mounted retractably within an insulative electrode head 118. Each of the electrodes is coupled to one of the coiled conductors within lead body 112. Electrodes 114 and 116 are employed for atrial pacing and for sensing atrial depolarizations. Elongated coil electrode 120 is provided proximal to electrode 114 and coupled to the third conductor within lead body 112. Electrode 120 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 122 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 124 carrying one coiled conductor coupled to an elongated coiled defibrillation electrode 126. Electrode 126, illustrated in broken outline in FIG. 4, is located within the coronary sinus and great vein of the heart. At the proximal end of the lead is connector plug 128 carrying an electrical connector coupled to the coiled conductor. Elongated coil defibrillation electrode 126 may be about 5 cm in length.

IMD 10 is shown in FIG. 4 in combination with leads 100, 112 and 124, and lead connector assemblies 110, 122 and 128 inserted into connector module 12. Optionally, insulation of the outward facing portion of housing 14 of IMD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of IMD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 150 in FIG. 5 includes the uninsulated portion of the housing of IMD 10. Electrodes 108, 118, 126 and 150 are coupled to high voltage output circuit 152, which includes high voltage switches controlled by CV/defib control logic 154 via control bus 156. Switches disposed within circuit 152 determine which electrodes are employed and which electrodes are coupled to the positive and negative terminals of a capacitor bank (which includes capacitors 158 and 160) during delivery of defibrillation pulses.

Electrodes 102 and 104 are located on or in the ventricle of the patient and are coupled to the R-wave amplifier 162, which preferably takes the form of an automatic gain controlled amplifier providing an adjustable sensing threshold as a function of the measured R-wave amplitude. A signal is generated on R-out line 165 whenever the signal sensed between electrodes 102 and 104 exceeds the present sensing threshold.

Electrodes 114 and 116 are located on or in the atrium of the patient and are coupled to the P-wave amplifier 164, which preferably also takes the form of an automatic gain controlled amplifier providing an adjustable sensing threshold as a function of the measured P-wave amplitude. A signal is generated on P-out line 167 whenever the signal sensed between electrodes 114 and 116 exceeds the present sensing threshold. The general operation of R-wave and P-wave amplifiers 162 and 164 may correspond to that disclosed in U.S. Pat. No. 5,117,824 to Keimel et al., hereby incorporated by reference herein in its entirety.

Switch matrix 166 is used to select which of the available electrodes are coupled to wide band (0.5–200 Hz) amplifier 168 for use in digital signal analysis. Selection of electrodes is controlled by microprocessor 170 via data/address bus 172, which selections may be varied as desired. Signals from the electrodes selected for coupling to bandpass amplifier 168 are provided to multiplexer 174, and thereafter converted to multi-bit digital signals by A/D converter 176, for storage in random access memory 178 under control of direct memory access circuit 180. Microprocessor 170 may employ digital signal analysis techniques to characterize the digitized signals stored in random access memory 178 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 182 preferably includes programmable digital counters which control the basic time intervals associated with DDD, VVI, DVI, VDD, AAI, DDI and other modes of single and dual chamber pacing well known to the art. Circuitry 182 also preferably controls escape intervals associated with anti-tachyarrhythmia pacing in both the atrium and the ventricle, employing any anti-tachyarrhythmia pacing therapies known to the art.

Intervals defined by pacing circuitry 182 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 170, in response to stored data in memory 178 and are communicated to pacing circuitry 182 via address/data bus 172. Pacer circuitry 182 also determines the amplitude of the cardiac pacing pulses under control of microprocessor 170.

During pacing, escape interval counters within pacer timing/control circuitry 182 are reset upon sensing of R-waves and P-waves as indicated by a signals on lines 165 and 167, and in accordance with the selected mode of pacing on time-out trigger generation of pacing pulses by pacer output circuitry 184 and 186, which are coupled to electrodes 102, 104, 112 and 116. Escape interval counters are also reset on generation of pacing pulses and thereby control the basic timing of cardiac pacing functions, including anti-tachyarrhythmia pacing. The durations of the intervals defined by escape interval timers are determined by microprocessor 170 via data/address bus 172. The value of the count present in the escape interval counters when reset by sensed R-waves and P-waves may be used to measure the durations of R-R intervals, P-P intervals, P-R intervals and R-P intervals, which measurements are stored in memory 178 and used to detect the presence of tachyarrhythmias.

Microprocessor 170 most preferably operates as an interrupt driven device, and is responsive to interrupts from pacer timing/control circuitry 182 corresponding to the occurrence of sensed P-waves and R-waves and corresponding to the generation of cardiac pacing pulses. Those interrupts are provided via data/address bus 172. Any necessary mathematical calculations to be performed by microprocessor 170 and any updating of the values or intervals controlled by pacer timing/control circuitry 182 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The rate of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al., and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May–June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 170 into the pacer timing and control circuitry 182 via data bus 172, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al., U.S. Pat. No. 4,880,005, issued to Pless et al., U.S. Pat. No. 4,726,380, issued to Vollmann et al., and U.S. Pat. No. 4,587,970, issued to Holley et al., all of which are incorporated herein by reference in their entireties, may also be employed.

In the event that generation of a cardioversion or defibrillation pulse is required, microprocessor 170 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 170 activates cardioversion/defibrillation control circuitry 154, which initiates charging of high voltage capacitors 158 and 160 via charging circuit 188, under the control of high voltage charging control line 190. The voltage on the high voltage capacitors is monitored via VCAP line 192, which is passed through multiplexer 174 and in response to reaching a predetermined value set by microprocessor 170, results in generation of a logic signal on Cap Full (CF) line 194 to terminate charging. Thereafter, timing of the delivery of the defibrillation or cardioversion pulse is controlled by pacer timing/control circuitry 182. Following delivery of the fibrillation or tachycardia therapy microprocessor 170 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al., and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 152 under the control of control circuitry 154 via control bus 156. Output circuit 152 determines whether a monophasic or biphasic pulse is delivered, the polarity of the electrodes and which electrodes are involved in delivery of the pulse. Output circuit 152 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877 to Kallok, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al., or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

FIG. 6 is a perspective view of programmer unit 200 which includes the present invention. Programmer unit 200 has various features, including outer housing 202, carrying handle 204, articulate display screen 206, RF head or stylus 208, and analyzer 210.

Display unit 206 is disposed on the upper surface of housing 202. Display screen 206 folds down in a closed position when programmer 200 is not in use, thereby reducing the size of programmer 200 and protecting the display surface of display screen 206 during transportation and storage. In the perspective view of FIG. 6, programmer 200 is shown with articulate display screen 206 having been lifted up into one of a plurality of possible open positions such that the display area is visible to a user situated in front of programmer 200. Display screen 206 is preferably an LCD or electroluminescent type, characterized by being relatively thin as compared to a cathode ray tube display, or the like. Display screen 206 is operatively coupled to computer circuitry disposed within housing 202 and is adapted to provide a visual display of graphics and/or numerical and alphanumeric data under control of the computer circuitry.

In accordance with one aspect of the present invention, display screen 206 is provided with touch-sensitivity capability, such that a user can interact with the internal computer by touching the display area of display screen 206 with stylus 208. It is believed that those of ordinary skill in the computer will be familiar with touch-sensitivity display technology, and the details of implementation of such display will not be described further herein. Display screen 206 is the primary input medium for programmer 200, and therefore preferably has sufficient resolution to support operations including selection, gestures, annotation, and character recognition.

Analyzer 210, which in prior art devices was a separate unit capable of connection to programmer unit 200 only via connecting cables, provides a medium for an operator to run a series of diagnostic tests during an implantation procedure of an IMD, such as IMD 10 previously discussed. For example, a continuous-time waveform or a single complex waveform can be analyzed by analyzer 210 and displayed on display screen 206 from a variety of implanted leads, such as a lead positioned in an atrium or ventricle of heart 8 (shown in FIGS. 1, 2 and 4).

Figure 7:
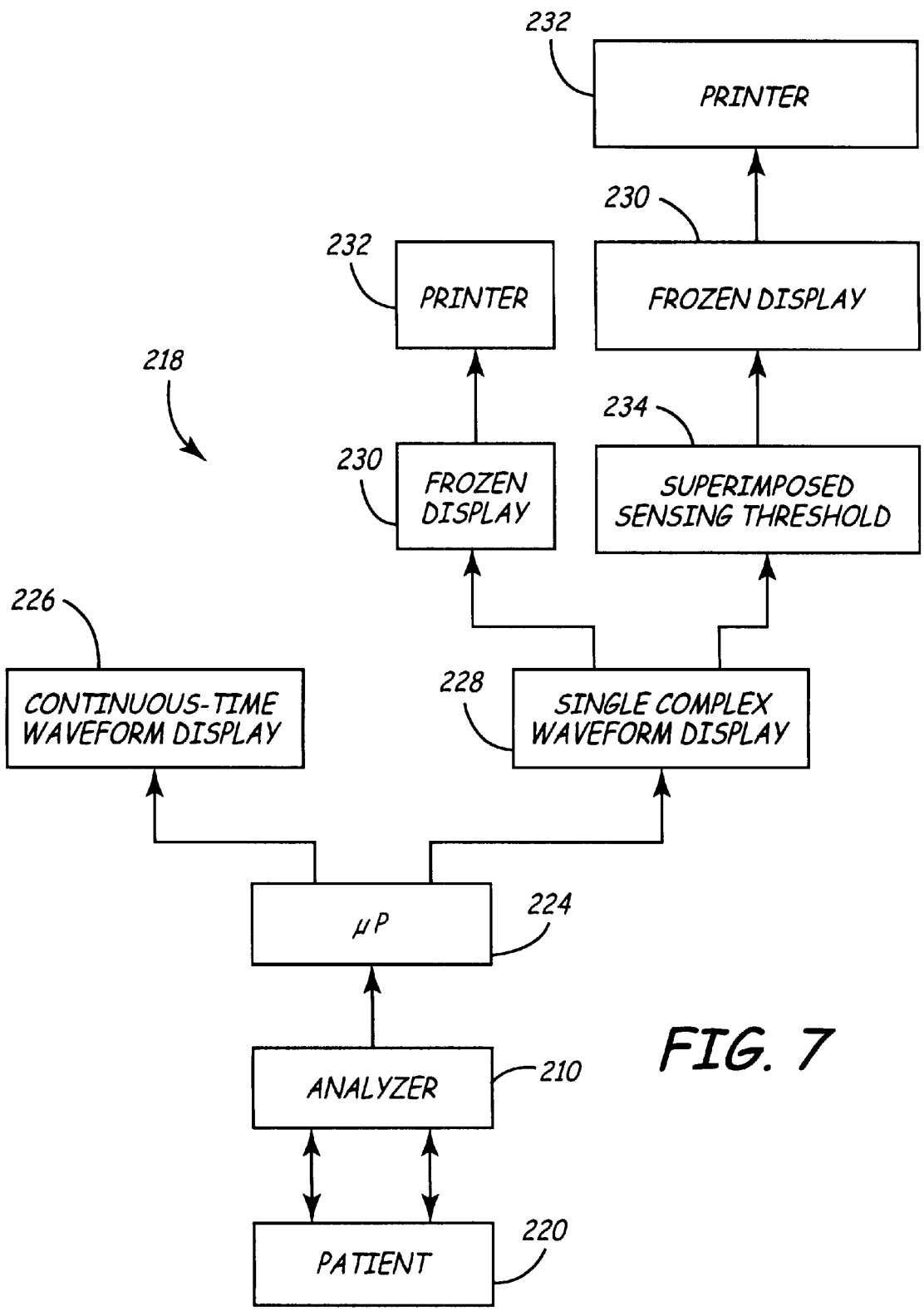
FIG. 7 is a block diagram encompassing the present invention.

FIG. 7 shows block diagram 218 encompassing various features of the present invention. Analyzer 210, as previously discussed, provides a medium for an operator to run a series of diagnostic tests during an implantation procedure of an IMD, such as IMD 10. Analyzer 210 receives a "raw" cardiac electrogram signal from the leads used to later connect IMD 10 to heart 8 of patient 220. Analyzer 210 includes a marker channel telemetry system which utilizes latches to store event information and forms marker codes. The marker codes indicate the occurrence of specific events such as sensed and paced events found in the electrogram signal, for example, the occurrence of a P-wave. Thus, analyzer 210 conditions the electrogram signal received from patient 210 by inserting markers into the electrogram signal. Examples of a marker channel telemetry system are disclosed in U.S. Pat. No. 4,374,382 to Markowitz, hereby incorporated by reference herein in its entirety.

The marker signal is supplied from analyzer 210 to microprocessor 224. Microprocessor 224 performs numerous functions with the received marked electrogram signal. One such function is the addition of amplitude information to the marked electrogram signal. Another function performed by microprocessor 224 is the continual reading of the marked electrogram signal. Microprocessor 224 performs a routine which monitors the content of the continuous electrogram signal for marker information. If a marker is detected that indicates the start of a cardiac waveform complex (P-wave), the information (the "raw" signal accompanied by the additional information) in the continuous signal proceeding the marker and following the marker is captured into a display buffer.

An operator, utilizing programmer unit 200, shown in FIG. 6, has a choice between displaying one or more continuous-time waveforms or displaying a single complex waveform. For purposes of this application, a single complex waveform is defined as a portion of the continuous-time waveform immediately before and after a marker. If a continuous waveform is chosen, microprocessor 224 enables continuous-time waveform display 226. Conversely, if a single complex waveform is desired, microprocessor 224 enables single complex waveform display 228.

When operating in the continuous-time waveform mode, continuous-time waveform display 226 is activated. An example of what is displayed on display screen 206 in this mode is shown in FIGS. 8 and 9.

Figure 8:
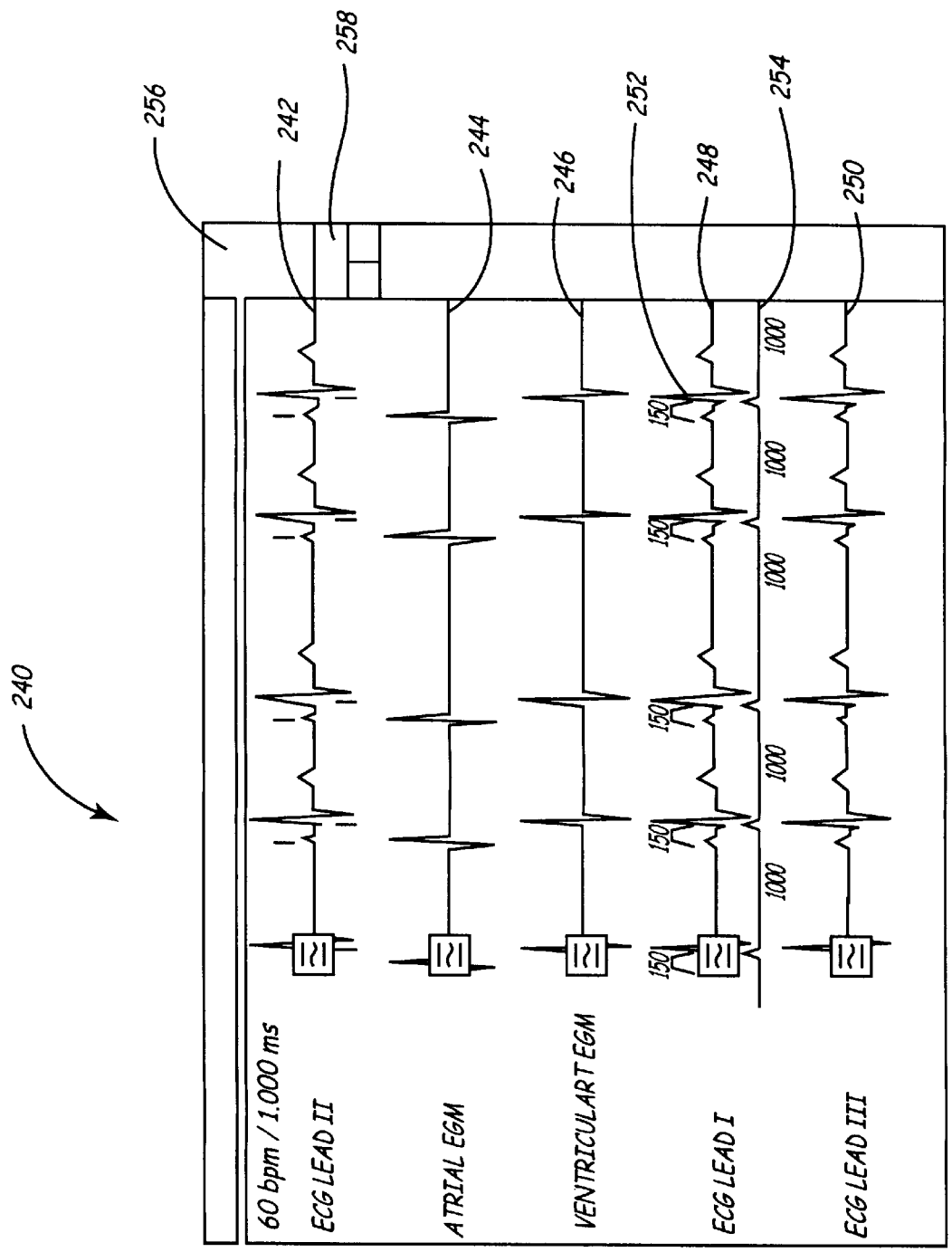
FIG. 8 is a pictorial representation of a typical display screen during an implant procedure showing a plurality of continuous-time waveforms.

FIG. 8 shows various signals 242, 244, 246, 248, and 250 which are continuously scrolling across the display screen from left to right. Display 240 of FIG. 8 also shows timing information 252 and 254 to assist an operator in evaluating the various waveforms, as well as toolbar 256. Toolbar 256 includes freeze button 258, continuous-time waveform icon 260, single complex cardiac waveform 262, and other features not relevant to the present invention. While toolbar 256 is shown in FIGS. 8–11 on the right portion of display screen 206, it is done for illustrative purposes only and the location of the toolbar 256 can be altered without deviating from the present invention.

Figure 9:
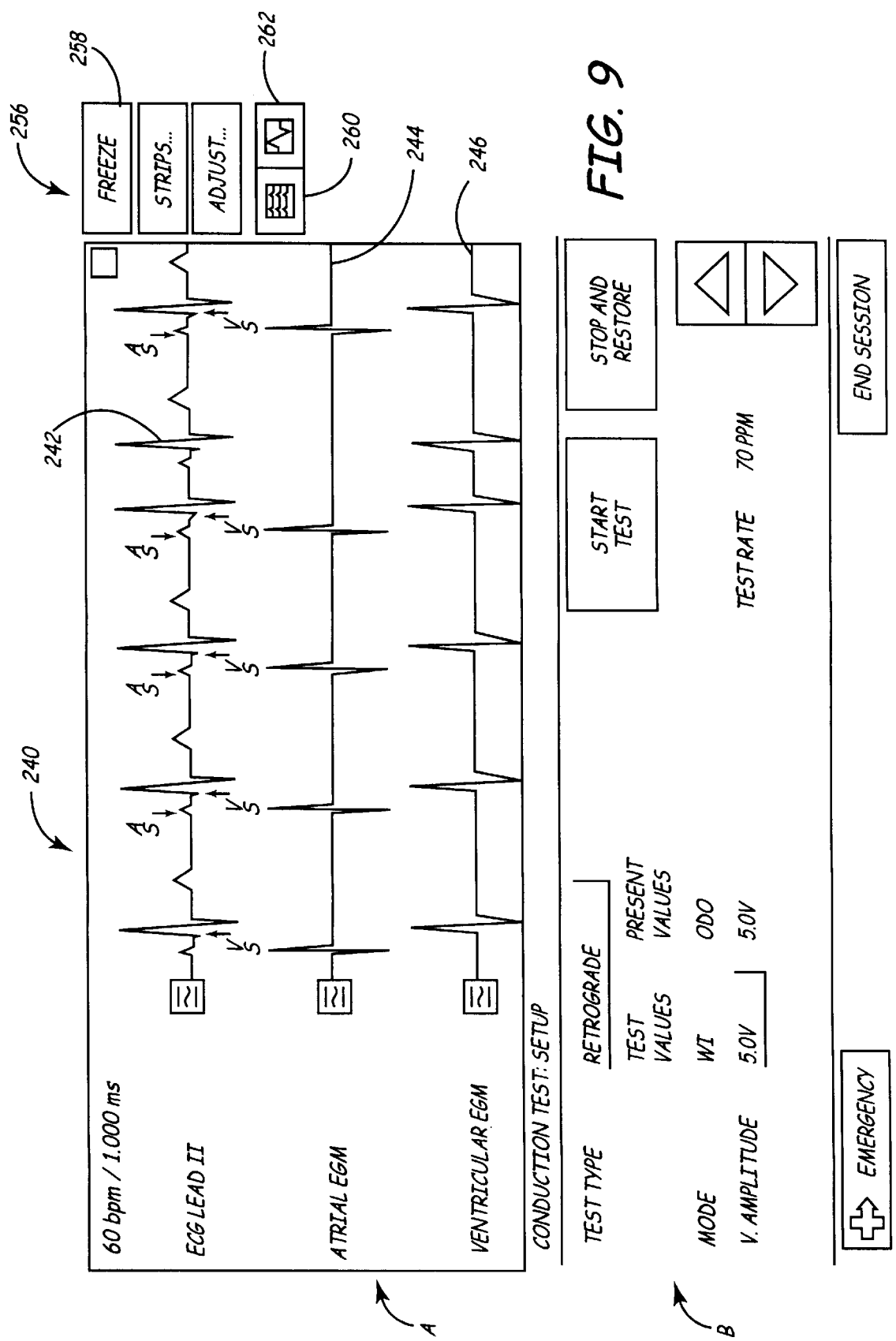
FIG. 9 is a second pictorial representation of a typical display screen during an implant procedure showing a waveform area and waveform control area.

FIG. 9 differs from FIG. 8 in that display screen 206 has been divided into two separate compartments, specifically continuous-time mode display 26A and continuous-time mode control 26B. Through utilization of continuous-time display control 264B, an operator can reprogram various aspects of programmer 200 and view the corresponding change in waveforms via continuous-mode display 264A.

During an implantation procedure, wherein an implantable medical device, such as a pacemaker, is implanted into patient 220, a prior art display screen would display continuous signals, such as those shown in FIGS. 8 and 9, constantly scrolling across display screen 206. Due to the constant movement of the signals across display screen 206, it is extremely difficult for an operator to analyze this information to determine if a pacing or sensing lead is properly positioned within a passageway of a patient.

Figure 10:
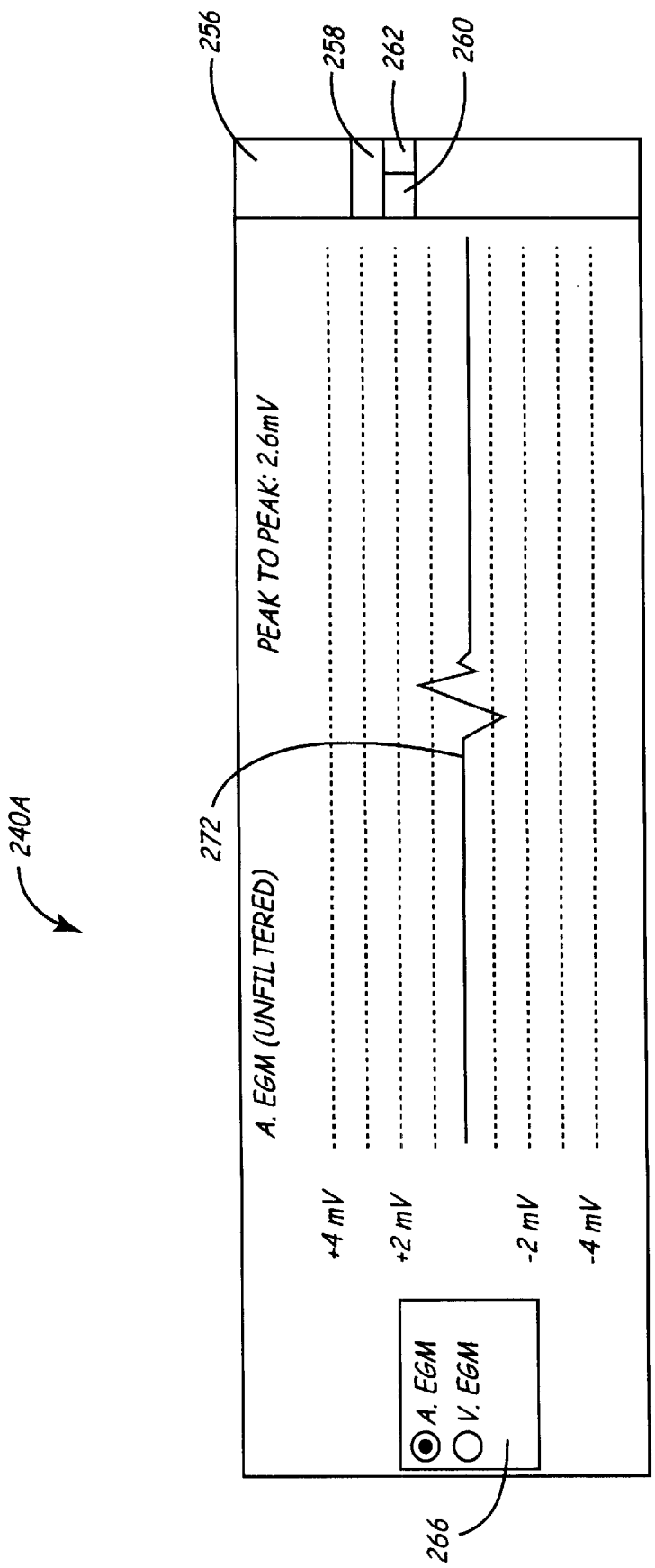
FIG. 10 is a pictorial representation of a display screen during an implant procedure showing a single complex cardiac waveform.

FIG. 10 discloses display 240A showing a graph of single complex waveform 272 representative of a portion of one of the continuous-time waveforms shown in FIGS. 8 and 9. Waveform 272 is shown in a time-expanded format so that the shape of waveform 272 can be analyzed. Additionally, amplitude information is displayed for greater analysis.

When operating in the single complex waveform mode, single complex waveform display 228 of FIG. 7 is activated and display screen 206 of programmer unit 200 displays a portion of the received electrogram signal corresponding to the information in the stream immediately preceding and following a marker. This information is centered on display screen 206. An example of what is displayed on display screen 206 is shown in FIG. 10. Microprocessor 224 continuously updates displayed waveform 272 at regular intervals. Specifically, microprocessor 224 will provide an updated waveform to display screen 206 stored in a display buffer within microprocessor 224 at regular intervals.

One aspect of the present invention is to provide a readable single complex waveform representing a portion of the received electrogram signal adjacent a marker which can be analyzed by the operator. The single complex waveform must be displayed in a constant location on display screen 206 and updated at a rate which can be processed by the operator. Thus, with the present invention, microprocessor 224 monitors a heart rate of the patient. If the heart rate is less than 90 beats per minute, the single cardiac waveform is updated with each heartbeat. If the heartbeat of the patient is between 90 and 160 heartbeats per minute, the single cardiac waveform is updated every other heartbeat, and if the patient's heartbeat is greater than 160 beats per minute, the single complex waveform is updated every third heartbeat.

Figure 11:
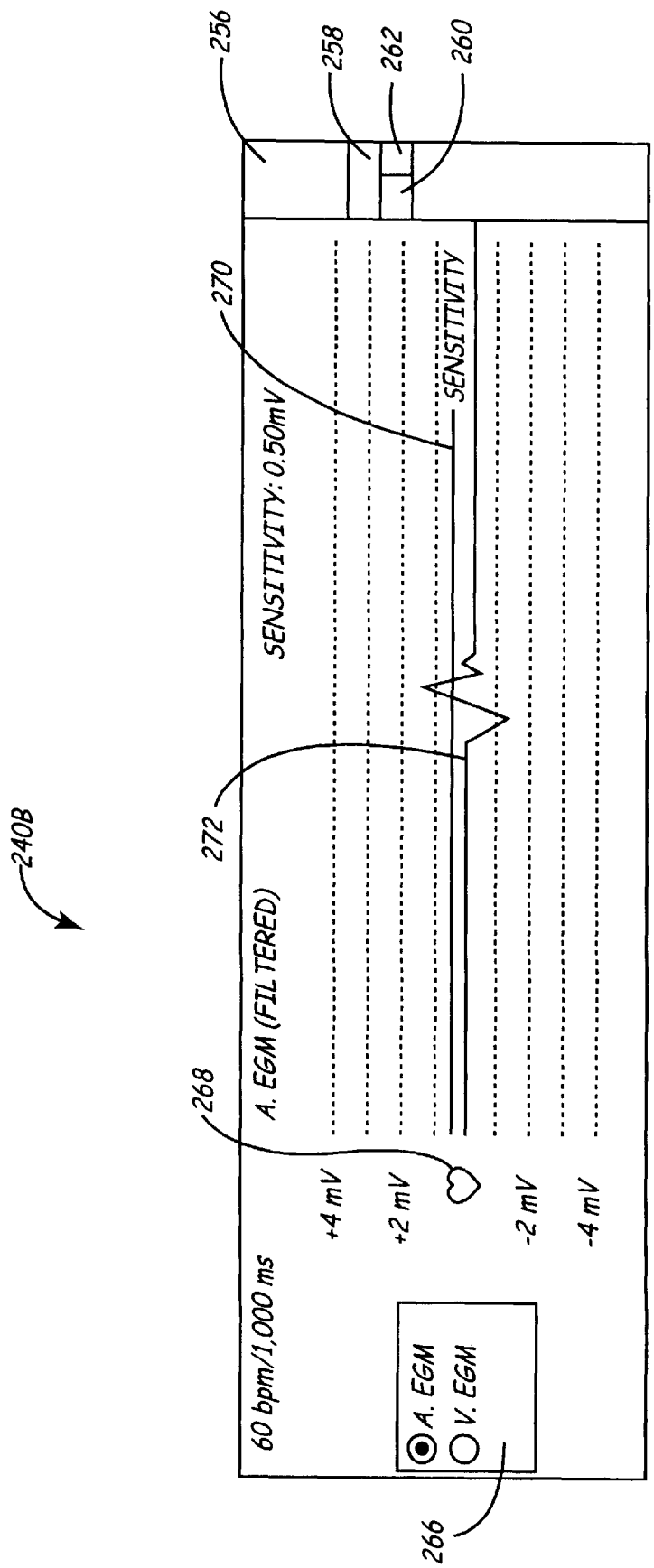
FIG. 11 is a second pictorial representation of a display screen during an implant procedure showing a single complex cardiac waveform.

Single complex waveform display 228 (of FIG. 7), which is displayed on display screen 206 in FIGS. 10 and 11, provides a means for an operator to evaluate the shape of a waveform, as well as its magnitude, thus enabling an operator to determine if a specific lead is properly positioned within a passageway of heart 8, during an implant procedure.

An additional feature of the present invention includes frozen display 230 (shown in FIG. 7). Frozen display 230 permits a user to "freeze" or hold a particular single complex waveform on display screen 206 for detailed evaluation via freeze button 258 (of FIGS. 10 and 11). The user can also print out the frozen display via printer 232.

With the present invention, the operator may utilize icons 260 and 262, shown in FIGS. 8 and 9, to facilitate a proper reading of the displayed signals. In accordance with the present invention, single complex waveform icon 262 permits a user to view a portion of a single displayed waveform corresponding to a single heartbeat of the patient. By utilizing icon 262, display screen 206 will display the graph shown in FIG. 10. During an implant procedure, it is desirous to view a single waveform corresponding to a single lead in order to determine proper location of the lead. An operator can modify the position of a specific lead and analyze a time, expanded continuously updated waveform. The configuration of the waveform aids the operator in determining the desired location of the lead. Continuous-time waveform icon 260 returns display screen 206 to the continuous-time waveform display.

As shown in FIG. 10, display 240A includes toolbar 256. Toolbar 256 further includes freeze icon 258, continuous-time waveform icon 260, and single complex cardiac waveform 262. As previously discussed, freeze icon 258 permits an operator to continuously view a specific waveform. Continuous-time waveform 260 and single complex waveform 262 act as a toggle switch which permits an operator to display the desired waveform. EGM panel 266 notifies the operator of the source of the signal being viewed, such as a signal from a lead within an atrium or ventricle of the patient, and permits switching between the two signals.

Figure 12:
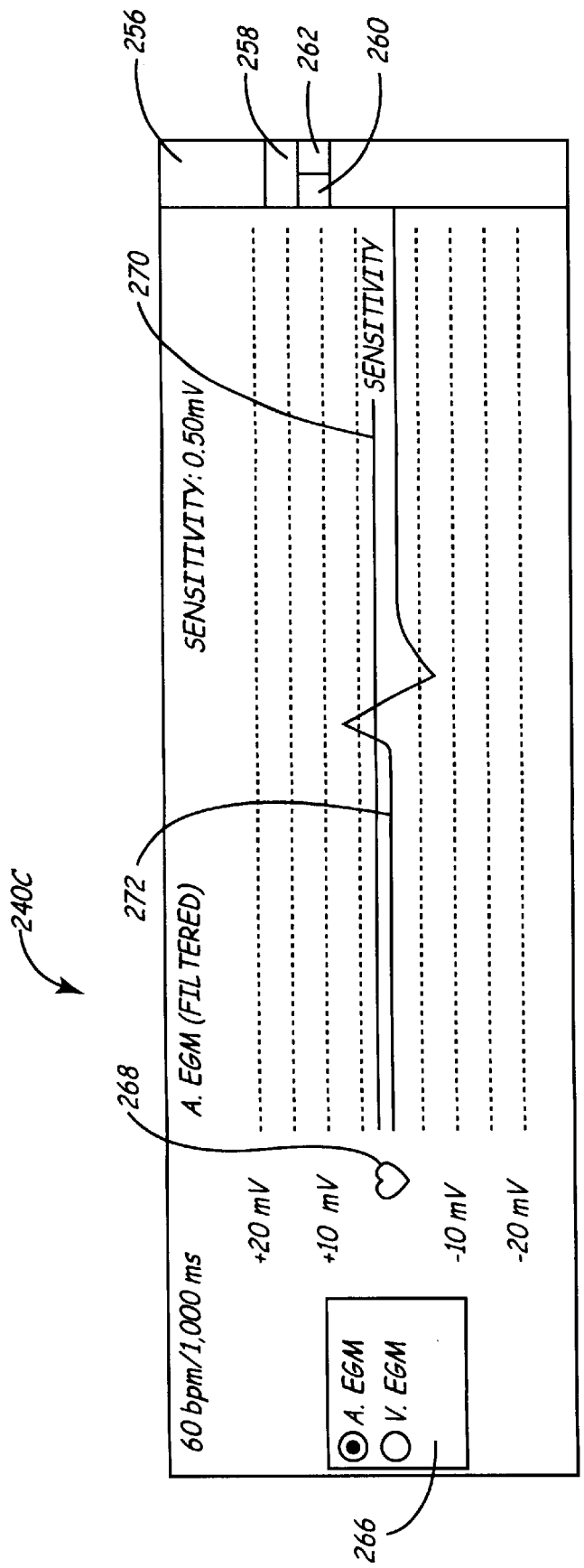
FIG. 12 is a third pictorial representation of a display screen during an implant procedure showing a single complex cardiac waveform.

FIGS. 11 and 12 shows display 240B and 240C which is virtually identical to display 240A shown in FIG. 10. However, the display shown in FIGS. 11 and 12 includes heartbeat icon 268 which will appear on display screen 206 each time a marker is sensed by microprocessor 224 representing a heartbeat. As previously discussed, waveform 272 will be updated every first, second, or third heartbeat depending upon the heart rate of the patient. If the heart rate of the patient is less than 90 beats per minute, signal 272 will be updated with each heartbeat. If the heart rate of the patient is between 90 and 160 beats per minute, signal 272 will be updated every other heartbeat. If the heart rate of the patient is greater than 160 beats per minute, waveform 272 will be updated every third heart beat.

An additional feature of the present invention is the ability of an operator to graphically assess the relationship of cardiac events to a sensitivity threshold of IMD 10, thereby providing a means to assess the degree of sensing margin for detected atrial and ventricular events. This feature is also is useful for assessing the degree of margin available for rejecting non-desired events, such as far-field signals and ventricular t-waves. More specifically, the present invention provides a graphical display of the sensitivity threshold, shown in FIGS. 11 and 12 as sensitivity threshold line 270. Sensitivity threshold line 270 is positioned at the graphical location representing a predetermined and adjustable voltage. Prior art references fail in their teachings to disclose a graphical display of the sensitivity threshold positioned across a display screen and in conjunction with a beat of a waveform, as shown in FIGS. 11 and 12.

It is critical that later implanted IMD 10, through its pacing and sensing leads, is capable of properly detecting electrical impulses from heart 8 of a patient, while filtering out unwanted noise, such as far-field signals. Later implanted IMD 10 must sense the intrinsic activity of heart 8 in order to properly operate.

As shown in FIGS. 11 and 12, waveform 272, which represents a simulated electrical signal simulating a heartbeat of a patient, has a positive peak point which is greater than sensitivity threshold line 270. In determining whether the sensitivity threshold of a particular unit is properly set, an operator would review the graphical representation shown in FIGS. 11 and 12. For proper location, the peak of electrical signal 272 must have a voltage greater than sensitivity threshold line 270. However, if sensitivity threshold line 270 is set at too low of a voltage, unwanted noise will be detected and a later implanted IMD may not function properly. The sensitivity threshold can be adjusted to correspond to a desired output through use of a display control, such as display control 264B, shown in FIG. 9. In FIG. 11, the sensitivity threshold is set at 0.50 millivolts, while in FIG. 12, the sensitivity threshold is set at 2.50 millivolts. In both instances (FIGS. 11 and 12), the sensitivity threshold is adequately set since the peak of electrical signal 272 has a voltage greater than sensitivity threshold line 270, but sensitivity threshold line 270 is not positioned to low to allow unwanted noise.

Figure 13:
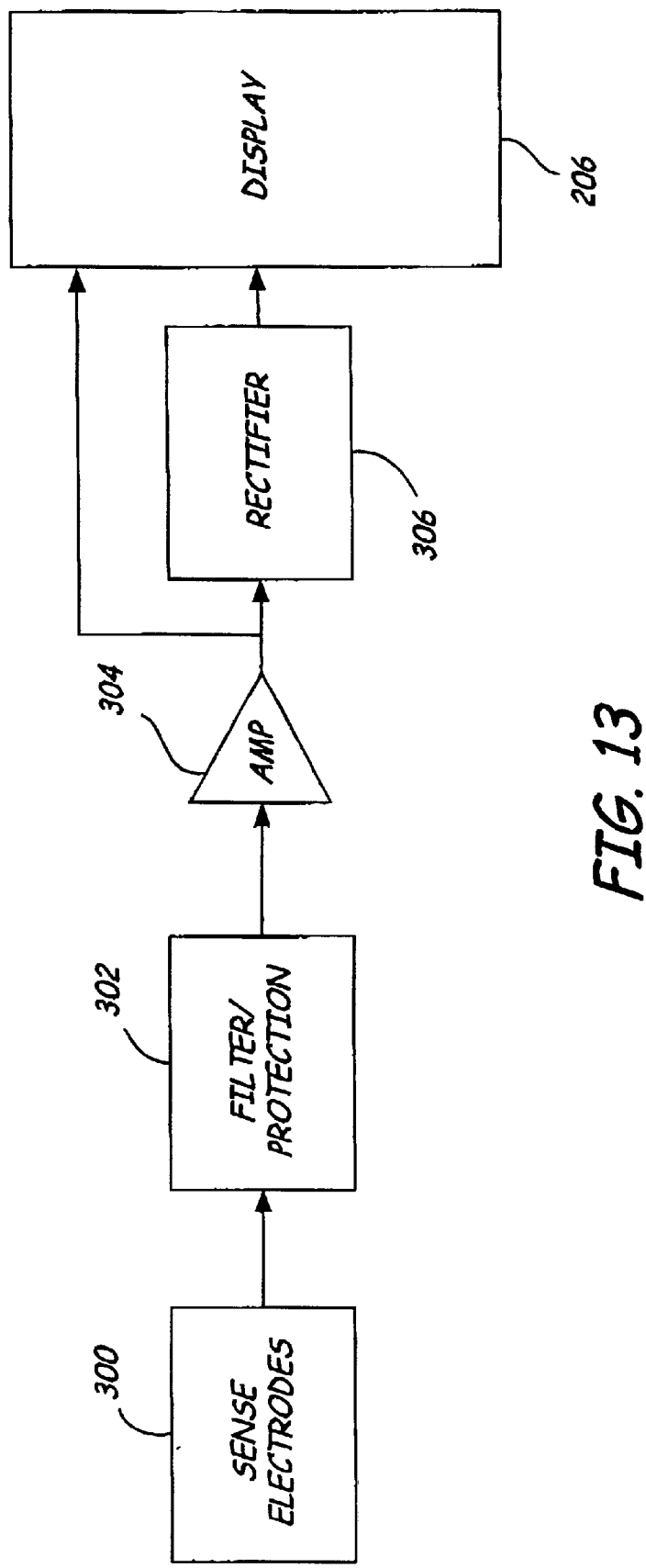
FIG. 13 is a flow chart disclosing the steps of the sensitivity threshold feature of the present invention.

FIG. 13 is a flow chart disclosing the steps encompassing the sensitivity threshold feature of the present invention. The elements shown and described in FIG. 13 are located within a programmer unit 200 (shown in FIG. 6). Electrode 300 would be attached to a specific sensing or pacing lead needing diagnostic evaluation. Filter/protection 302 would receive a signal from sense electrode 300. The purpose of filter/protection 302 is to simulate the characteristics of the input sensing portion of IMD 10. This ensures that the sensing characteristics being analyzed will correspond with the sensing characteristics of later implanted IMD 10. Amplifier 304 receives a signal from filter/protection 302 and provides an amplified signal to either display 206 or rectifier 306. Thus, display 206 can display either a rectified or non-rectified sensitivity threshold.

In the claims, means-plus-function clauses are intended to cover the structures described herein as performing the reciting function and not only structural equivalence but also equivalent structures. For example, although a nail and a screw may not be structurally equivalent in that a nail employs a cylindrical surface to secure wooden parts together, whereas a screw employs a helical surface, in the environment of fastening wood parts, a nail and a screw are equivalent structures.

Although specific embodiments of the invention have been set forth herein in some detail, it is understood that this has been done for the purposes of illustration only and is not to be taken as a limitation on the scope of the invention as defined in the appended claims. It is to be understood that various alterations, substitutions, and modifications may be made to the embodiment described herein without departing from the spirit and scope of the appended claims.

What is claimed is:

1. A system for graphically displaying information received from at least one lead positioned within a passageway of a heart related to an implantable medical device, the system comprising:

an analyzer for receiving the electrogram signal from the electrical lead and for locating and marking desired characteristics of the electrogram signal with a plurality of markers to produce a marked electrogram signal;

a processor for receiving the marked electrogram signal from the analyzer, for recognizing the marked desired characteristics of the electrogram signal, and for inserting amplitude information into the marked electrogram signal;

a display buffer for momentarily capturing a portion of the electrogram signal adjacent to a single marker;

updating means for continuously updating the captured portion of the electrogram signal;

a selection switch for selecting a selected signal between the electrogram signal received from the electrical lead and the captured portion of the electrogram signal stored in the display buffer;

a sensitivity threshold control for controlling a sensitivity threshold; and a display controlled by the processor for displaying the selected signal and for graphically displaying the sensitivity threshold superimposed on the selected signal.

2. The system of claim 1, wherein the processor centers the selected signal on the display.

3. The system of claim 1, wherein the processor displays the amplitude information on the display.

4. The system of claim 1, wherein the processor further comprises:

monitoring means for monitoring a heart rate; and comparing means for comparing the heart rate to a predetermined set of ranges.

5. The system of claim 4, wherein the updating means updates the captured portion of the electrogram signal with every heartbeat.

6. The system of claim 4, wherein the updating means updates the captured portion of the electrogram signal with every second heartbeat.

7. The system of claim 4, wherein the updating means updates the captured portion of the electrogram signal with every third heart beat.

8. The system of claim 1 and further comprising a hold icon located on the display and controlled by the processor for holding the selected signal and the sensitivity threshold on the display.

9. The system of claim 8 and further comprising a print icon located on the display and controlled by the processor for printing the selected signal and the sensitivity threshold held on the display.

10. The system of claim 1, wherein the display displays the selected signal and the sensitivity threshold in a time-expanded format.

11. A programmer for graphically displaying information received from at least one lead positioned within a passageway of a heart and related to an implantable medical device, the programmer comprising:

an analyzer for receiving an electrogram signal and for locating and marking desired characteristics of the electrogram signal with a plurality of markers to produce a marked electrogram signal;

a processor for receiving the electrogram signal from the analyzer and for recognizing the marked desired characteristics of the electrogram signal, the processor also receiving sensitivity threshold information; and a display controlled by the processor for graphically displaying information representing a portion of the electrogram signal immediately adjacent to a single marker and for graphically displaying a sensitivity threshold.

12. The programmer of claim 11, wherein the processor centers the portion of the electrogram signal immediately adjacent to a single marker on the display.

13. The programmer of claim 11, wherein the processor inserts amplitude information onto the electrogram signal.

14. The system of claim 13, wherein the processor displays the amplitude information on the display.

15. The programmer of claim 11, wherein the processor further comprises:
monitoring means for monitoring a heart rate; and
comparing means for comparing the heart rate to a predetermined set of ranges.

16. The programmer of claim 15, wherein the display displays an updated portion of the electrogram signal immediately adjacent to a single marker with every heartbeat.

17. The programmer of claim 15, wherein the display displays an updated portion of the electrogram signal immediately adjacent to a single marker with every second heartbeat.

18. The programmer of claim 15, wherein the display displays an updated portion of the electrogram signal immediately adjacent to a single marker with every third heartbeat.

19. The programmer of claim 11, and further comprising a hold icon located on the display and controlled by the processor for holding the electrogram signal immediately adjacent to a single marker and for holding the sensitivity threshold.

20. The programmer of claim 19, and further comprising a print icon located on the display and controlled by the processor for printing the portion of the electrogram signal immediately adjacent to a single marker and for printing the sensitivity threshold.

21. The programmer of claim 11, further comprising a user input, wherein the processor receives updated sensitivity threshold information based upon an input from a user.

22. A method of graphically displaying information relating to an electrogram signal received from at least one lead positioned within a passageway of a heart and related to an implantable medical device, the programmer comprising:
analyzing the electrogram signal to locate desired characteristics of the electrogram signal;
inserting a plurality of markers into the electrogram signal at a location of the desired characteristics;
filtering a sensitivity threshold signal received from a lead to remove unwanted noise;
amplifying the filtered sensitivity threshold signal; and
displaying a portion of the electrogram signal immediately adjacent to a single marker and graphically displaying a sensitivity threshold level representing the amplified and filtered sensitivity threshold signal.

23. The method of claim 22, wherein the step of displaying a portion of the electrogram signal further comprises:
centering the portion of the electrogram signal immediately adjacent to a single marker on the display.

24. The method of claim 22 and further comprising:
inserting amplitude information into the electrogram signal.

25. The method of claim 24, wherein the step of displaying a portion of the electrogram signal further comprises:
displaying the amplitude information.

26. The method of claim 22 and further comprising:
monitoring a heart rate; and
comparing the heart rate to a predetermined range.

27. The method of claim 26 and further comprising:
displaying the portion of the electrogram signal immediately adjacent to a single marker after each heartbeat.

28. The method of claim 26 and further comprising:
displaying the portion of the electrogram signal immediately adjacent to a single marker after every second heartbeat.

29. The method of claim 26 and further comprising:
displaying the portion of the electrogram signal immediately adjacent to a single marker after every third heartbeat.

30. The method of claim 22 and further comprising:
maintaining the displayed portion of the electrogram signal and the sensitivity threshold level on the display.

31. The method of claim 22 and further comprising:
printing the displayed portion of the electrogram signal and the sensitivity threshold level.

\* \* \* \* \*